United States Patent
Hoare et al.

(10) Patent No.: US 10,183,676 B2
(45) Date of Patent: Jan. 22, 2019

(54) SYSTEM FOR USE IN A VEHICLE

(71) Applicant: Jaguar Land Rover Limited, Coventry, Warwickshire (GB)

(72) Inventors: Edward Hoare, Malvern (GB); Thuy-Yung Tran, Rugby (GB); Marina Gashinova, Birmingham (GB); Aleksandr Bystrov, Birmingham (GB); Mikhail Cherniakov, Birmingham (GB)

(73) Assignee: JAGUAR LAND ROVER LIMITED, Warwickshire (GB)

( * ) Notice: Subject to any disclaimer, the term of this patent is extended or adjusted under 35 U.S.C. 154(b) by 0 days.

(21) Appl. No.: 15/118,401

(22) PCT Filed: Feb. 3, 2015

(86) PCT No.: PCT/EP2015/052151
§ 371 (c)(1),
(2) Date: Aug. 11, 2016

(87) PCT Pub. No.: WO2015/121107
PCT Pub. Date: Aug. 20, 2015

(65) Prior Publication Data
US 2017/0166214 A1    Jun. 15, 2017

(30) Foreign Application Priority Data

Feb. 12, 2014  (GB) .................................. 1402388.1

(51) Int. Cl.
*B60W 40/06*        (2012.01)
*G01S 13/86*        (2006.01)
(Continued)

(52) U.S. Cl.
CPC ............ *B60W 40/06* (2013.01); *G01N 29/11* (2013.01); *G01S 7/41* (2013.01); *G01S 7/539* (2013.01);
(Continued)

(58) Field of Classification Search
None
See application file for complete search history.

(56) References Cited

U.S. PATENT DOCUMENTS

| 2012/0287978 A1* | 11/2012 | O'Keeffe | ............ H01Q 21/245 375/222 |
| 2014/0257621 A1* | 9/2014 | Zych | .................. G01C 21/3453 701/25 |
| 2015/0212199 A1* | 7/2015 | Nakamura | .............. G01W 1/00 342/118 |

FOREIGN PATENT DOCUMENTS

| DE | 4200299 A1 | 7/1993 |
| EP | 0875749 A2 | 11/1998 |

(Continued)

OTHER PUBLICATIONS

Kees et al., "Road surface classification by using a polarmetric coherent radar module at millimeter waves," Microwave Symposium Digest, IEEE MTT-S International San Diego, CA, p. 1675, May 23, 1994.

(Continued)

*Primary Examiner* — Lail A Kleinman
(74) *Attorney, Agent, or Firm* — Miller Nash Graham & Dunn LLP

(57) ABSTRACT

A system for use in a vehicle for determining an indication of the type of terrain in the vicinity of the vehicle, the system comprising; means configured to receive sensor output data from at least one vehicle-mounted sensor (12, 22) which is configured to receive a reflected signal from the terrain; means configured to calculate at least two parameters from (Continued)

the sensor output data; means configured to convert the at least two parameters to a data point for a cluster model comprising a plurality of clusters of pre-determined data points, wherein each cluster corresponds to a different terrain type; and means configured to define to which one of the clusters the data point belongs, so as to determine an indication of the terrain type.

20 Claims, 7 Drawing Sheets

(51) Int. Cl.
  *G01S 7/539* (2006.01)
  *G01S 7/41* (2006.01)
  *G01N 29/11* (2006.01)
  *B60W 50/00* (2006.01)
  *G01S 7/02* (2006.01)
(52) U.S. Cl.
  CPC .... *G01S 13/862* (2013.01); *B60W 2050/0075* (2013.01); *B60W 2050/0083* (2013.01); *B60W 2050/0095* (2013.01); *B60W 2420/52* (2013.01); *B60W 2420/54* (2013.01); *B60W 2550/141* (2013.01); *B60W 2550/147* (2013.01); *B60W 2550/148* (2013.01); *G01N 2291/023* (2013.01); *G01N 2291/028* (2013.01); *G01N 2291/045* (2013.01); *G01N 2291/2638* (2013.01); *G01S 7/024* (2013.01)

(56) References Cited

FOREIGN PATENT DOCUMENTS

| | | |
|---|---|---|
| EP | 2216659 A1 | 8/2010 |
| KR | 20010047234 A | 6/2001 |

OTHER PUBLICATIONS

International Search Report and Written Opinion for International Patent Application No. PCT/EP2015/052151, dated May 7, 2015, 16 pages.

* cited by examiner

| Frequencies used for recognition | | Dimensionality (number of parameters) | | | | |
|---|---|---|---|---|---|---|
| | | 2 | 3 | 4 | 5 | 6 |
| 9 GHz | Optimal set of parameters | σvv, pvv | σvv, pvv, d | σvv, pvv, pvh, d | - | - |
| 9 GHz | Recognition probability | 0.79 | 0.86 | 0.88 | - | - |
| 18 GHz | Optimal set of parameters | σvv, pvv | σvv, pwv, d | σvv, pvv, pvh, d | - | - |
| 18 GHz | Recognition probability | 0.78 | 0.85 | 0.85 | - | - |
| 9 and 18 GHz | Optimal set of parameters | pvv, (9GHz), pvv(18GHz) | σvv(9Ghz), pvv(9GHz), pvv(18G Hz) | σvv(9Ghz), pvv(9GHz), σvv(18Ghz), pvv(18GHz) | σvv(9Ghz), pvv(9GHz), σvv(18GHz), pvv(18GHz), d(9GHz) | σvv(9Ghz), pvv(9GHz), σvv(18GHz), pvv(18GHz), d(9GHz), d(18GHz) |
| 9 and 18 GHz | Recognition probability $pr$ | 0.80 | 0.88 | 0.90 | 0.90 — 110 | 0.93 — 112 |

FIGURE 6

SYSTEM FOR USE IN A VEHICLE

CROSS-REFERENCE TO RELATED APPLICATIONS

This application is a 371 of International Application No. PCT/EP2015/052151, filed 3 Feb. 2015, which claims priority to GB Patent Application 1402388.1, filed 12 Feb. 2014, the contents of which are incorporated by reference herein in their entirety.

FIELD OF THE INVENTION

The present invention relates to a system for use in a vehicle and in particular to a system that enables a vehicle to determine an indication of the type of terrain in the vicinity of the vehicle. Aspects of the invention relate to a vehicle system, to a method for use in a vehicle, and to a vehicle itself.

BACKGROUND

Many modern vehicles are fitted with systems (anti-lock braking, adjustable ride height etc.) designed to improve the riding experience of the users. The riding experience could be a measure of, for example, vehicle composure or comfort, and the setup of the systems of a vehicle to optimise the riding experience can be dependent on the type of terrain over which the vehicle travels. Current systems have defined system configurations for a plurality of different terrain types. In a vehicle terrain response system (VTRS), such as Terrain Response®, the user may determine the terrain type over which the vehicle is travelling, or determine the terrain type ahead of the vehicle, and manually input this information into a vehicle control system (VCS) which then adjusts the configuration of the systems appropriately. Alternatively, the vehicle may be fitted with sensors designed to measure certain characteristics of vehicle subsystems (such as wheel acceleration, wheel slip, steering force estimator etc.) that are indicative of the terrain type over which the vehicle is travelling. Based on these measurements, the VTRS may determine the terrain type that most likely fits with these characteristics, and adjust the configuration of the systems appropriately, for example as described in GB patent application GB2492655. However, the determination of a terrain type by examining vehicle parameters using on-board systems is a reactive solution to the terrain over which the vehicle is currently travelling and as such does not allow the vehicle to prepare in advance for the terrain over which it is about to travel without user-input.

It is, however, desirable that a vehicle system could remotely determine the terrain type in the vicinity of the vehicle. This is desirable because the user controlling the vehicle may be unaware of possible hazards (slippery surfaces caused by water, ice, snow, wet grass etc.) in the vicinity and therefore it is necessary that either the vehicle prepares for the hazard automatically or the user controlling the vehicle is alerted. This is desirable also because automated moving devices (robots, unmanned vehicles, automatic aircraft landing systems etc.) are becoming increasingly important and do not have user-input available to prepare for the terrain in the vicinity.

Different types of vehicle-mounted sensors may be used to collect data for a plurality of different parameters indicative of the terrain over which the vehicle is currently travelling. The collected data for a particular terrain type may contain a reasonable amount of noise between readings. For example, the collected data for grass may vary depending on the length of the grass. The collected data may also contain outlying data points: this may be caused by, for example, objects on the terrain surface. It is desirable that, when determining a terrain type, a vehicle system can process collected data containing noise and outlying data points in such a way as to identify certain characteristics that relate to each terrain type. In addition, different parameters may show greater differences in the collected data between different terrain types in different situations. It is therefore also desirable that the vehicle system can deal with a large number of parameters, and select the optimal set of parameters with which to determine the terrain type.

One object of the present invention is to provide a vehicle system that is configured to process sensor output data to identify certain characteristics relating to a particular terrain type and to determine an indication of the terrain type in the vicinity of the vehicle based on these identified characteristics, that addresses the difficulties described above in such a way that the systems in the prior art cannot.

STATEMENTS OF THE INVENTION

According to an aspect of the invention there is provided a system for use in a vehicle for determining an indication of the type of terrain in the vicinity of the vehicle, the system comprising receiving means configured to receive sensor output data from at least one vehicle-mounted sensor which is configured to receive a reflected signal from the terrain, and calculating means configured to calculate at least two parameters from the sensor output data. "Vehicle-mounted" may mean a portable device carried on the vehicle temporarily. The system also includes converter means configured to convert the at least two parameters to a data point for a cluster model comprising a plurality of clusters of pre-determined data points, wherein each cluster corresponds to a different terrain type. The system further includes determining means configured to define to which one of the clusters the data point belongs, so as to determine an indication of the terrain type.

The receiving means, the calculating means, the converter means, and the determining means may comprise an electronic control unit or one or more controllers. The electronic controller, or the one or more controller may have, associated therewith, micro-processors programmed to execute the required functions. In addition the electronic controller, or the one or more controller, may have an internal, or associated external, memory means, for example a solid state memory device. It will be appreciated that all the functional "means" referred to throughout this document may be considered as control functions within one or more electronic control units or controllers.

The use of a cluster model to determine an indication of the terrain type in the vicinity of the vehicle is advantageous because it can cope with, or take account of the, wide variations in the values of the parameters between different sets of sensor output data that may correspond to a particular terrain type. The system may be used beneficially to determine the terrain type ahead of the vehicle i.e. by analysing sensor output data from sensors receiving a signal reflected from terrain ahead of the vehicle.

In one embodiment, the system comprises output means configured to output a control signal to one or more vehicle systems to automatically adjust the setup of the at least one vehicle subsystem according to the determined terrain type. The pre-determined data points may comprise empirically-gathered data and/or a standardised data set.

The system may be configured to enable communication of the determined terrain type to the user, for example the system may include a human machine interface (HMI). The system may be further configured to enable user-input of a terrain type following determination of the terrain type by the user, or to enable user confirmation of the determined terrain type following determination of the terrain type by the system.

In an embodiment, the system comprises means configured to store the pre-determined data points, and further comprises means configured to output to the means configured to store the at least two parameters together with the corresponding determined terrain type as part of a self-learning process. The pre-determined data may therefore be added to and updated using real-time sensor output data, enhancing the prospect of the system accurately determining the terrain type in the vicinity of the vehicle.

In one embodiment, the system comprises comparator means configured to compare the determined terrain type with the terrain type determined by the user as part of a self-learning process. If the user can determine the terrain type in the vicinity of the vehicle and communicate the determined terrain type to this system, then this can act as a check or a correction to the system's determination of terrain type. The system may further comprise means configured to store the at least two parameters together with the corresponding terrain type as part of a self-learning process. In another embodiment, the system comprises comparator means configured to compare the determined terrain type with a terrain type as determined from one or more other vehicle-mounted sensor. Comparing the system's determination with one or both of the user's determination and the on-board sensors determination will lead to a system that is increasingly accurate in determining an indication of the terrain in the vicinity of the vehicle.

In one embodiment, the receiving means may be configured to receive a reflected radar signal from the terrain ahead of the vehicle. The receiving means may be configured to receive a reflected radar signal at a plurality of radar signal frequencies. Collecting sensor output data at a plurality of frequencies increases the number of independent parameters available to the system when determining the terrain type, thus improving the reliability of the results.

In one embodiment, the receiving means may be configured to receive a signal in the form of a received horizontally polarised signal representative of power in a received horizontal polarisation component of a radar signal reflected from the terrain ahead of the vehicle and/or to receive a vertically polarised signal representative of power in a received vertical polarisation component of a radar signal reflected from the terrain ahead of the vehicle. The calculating means may be further configured to determine one or more of: a horizontal polarisation power signal, that is the power of the received horizontally polarised signal from a horizontally polarised transmitter; a vertical polarisation power signal, that is the power of the received vertically polarised signal; and a cross polarisation power signal, that is the power of the received horizontally polarised signal from a vertically polarised transmitter or the power of the received vertically polarised signal from a horizontally polarised transmitter.

In one embodiment, the receiving means may be configured to receive a signal in the form of a received elliptically polarised signal, which may be a received circularly polarised signal. The calculating means may be further configured to determine a cross polarisation power signal, that is the power of a received clockwise-rotating elliptically polarised signal from a transmitted anticlockwise-rotating elliptically polarised signal, or the power of a received anticlockwise-rotating elliptically polarised signal from a transmitted clockwise-rotating elliptically polarised signal. There are certain types of terrain which are particularly sensitive to elliptically polarised signals and so this may prove to be a useful parameter when determining certain terrain types. Note from above that "cross polarisation" may refer to either the received horizontal (or vertical) signal from the transmitted vertical (or horizontal) signal or the received clockwise- (or anticlockwise-) rotating signal from the transmitted anticlockwise- (or clockwise-) rotating signal.

In one embodiment, the calculating means is configured to determine the ratio of any two of: the horizontal polarisation power signal; the vertical polarisation power signal; and the cross polarisation power signal. Use of the relative values obtained by determining the abovementioned ratios is advantageous over the use of absolute values of the parameters since relative values depend to a lesser extent on the signal power from a transmitter and also the distance from the transmitter to the target terrain.

In one embodiment, the receiving means may be configured to receive a reflected acoustic signal from the terrain ahead of the vehicle at one or more acoustic signal frequencies. The use of acoustic sensors may be preferable over radar sensors in certain situations, or the combination of both would further increase the number of independent parameters. The calculating means may be further configured to determine a ratio of the acoustic power signal and one or more of: the horizontal polarisation power signal; the vertical polarisation power signal; and the cross polarisation power signal.

In one embodiment, the determining means may be configured to calculate the distance between the data point relating to the at least two parameters and at least two of the pre-determined data points. This may be calculated using a Euclidean algorithm. The determining means may include one of: a 'k-nearest neighbour' algorithm; a 'k-means' algorithm; a 'classification tree' algorithm; a 'naïve Bayes' algorithm; and a 'support vector machine' algorithm.

The determining means may include using external data to eliminate certain clusters from consideration. External data may include data obtained from other sensors on the vehicle, such as an external temperature sensor, for example. This will assist in reducing computing time and improving the possibility of a correct determination.

According to another aspect of the invention, there is provided a method for implementing the system capabilities described above to enable the system to determine an indication of the terrain type in the vicinity of the vehicle.

In a further embodiment, there is provided a data memory containing a computer readable code for performing the method described above.

According to another aspect of the invention there is provided a vehicle controller for determining an indication of the type of terrain in the vicinity of the vehicle, the controller comprising an input to receive sensor output data from at least one vehicle-mounted sensor which is configured to receive a reflected signal from the terrain, and a processor to calculate at least two parameters from the sensor output data. "Vehicle-mounted" may mean a portable device carried on the vehicle temporarily. The processor also converts the at least two parameters to a data point for a cluster model stored in memory of or associated with the controller, the cluster model comprising a plurality of clusters of pre-determined data points, wherein each cluster corresponds to a different terrain type. The processor further defines to which one of the clusters the data point belongs, and thereby determines an indication of the terrain type.

The controller described herein can comprise a control unit or computational device having one or more electronic processors. The system may comprise a single control unit or electronic controller or alternatively different functions of the controller may be embodied in, or hosted in, different control units or controllers. As used herein the term "control unit" will be understood to include both a single control unit or controller and a plurality of control units or controllers collectively operating to provide the stated control functionality. A set of instructions could be provided which, when executed, cause said computational device to implement the control techniques described herein. The set of instructions could be embedded in said one or more electronic processors. Alternatively, the set of instructions could be provided as software to be executed on said computational device.

According to another aspect of the invention, there is provided a vehicle comprising a system, or controller as described above, and at least one vehicle-mounted sensor.

Within the scope of this application it is expressly envisaged that the various aspects, embodiments, examples and alternatives set out in the preceding paragraphs, in the claims and/or in the following description and drawings, and in particular the individual features thereof, may be taken independently or in any combination. For example, features disclosed in connection with one embodiment are applicable to all embodiments, except where such features are incompatible.

BRIEF DESCRIPTION OF DRAWINGS

The invention will now be described, by way of example only, with reference to the accompanying figures in which:

FIG. 6 shows a table of the optimal set of parameters of the sensor output data in FIG. 5 in the cases where the optimal set contains 2, 3, 4, 5 or 6 parameters, together with the probability that the terrain type is determined correctly in each case;

DETAILED DESCRIPTION

In one embodiment of the present invention, data relating to the terrain ahead of a vehicle is collected from at least one type of sensor on a vehicle for a plurality of different parameters.

Figure 1:
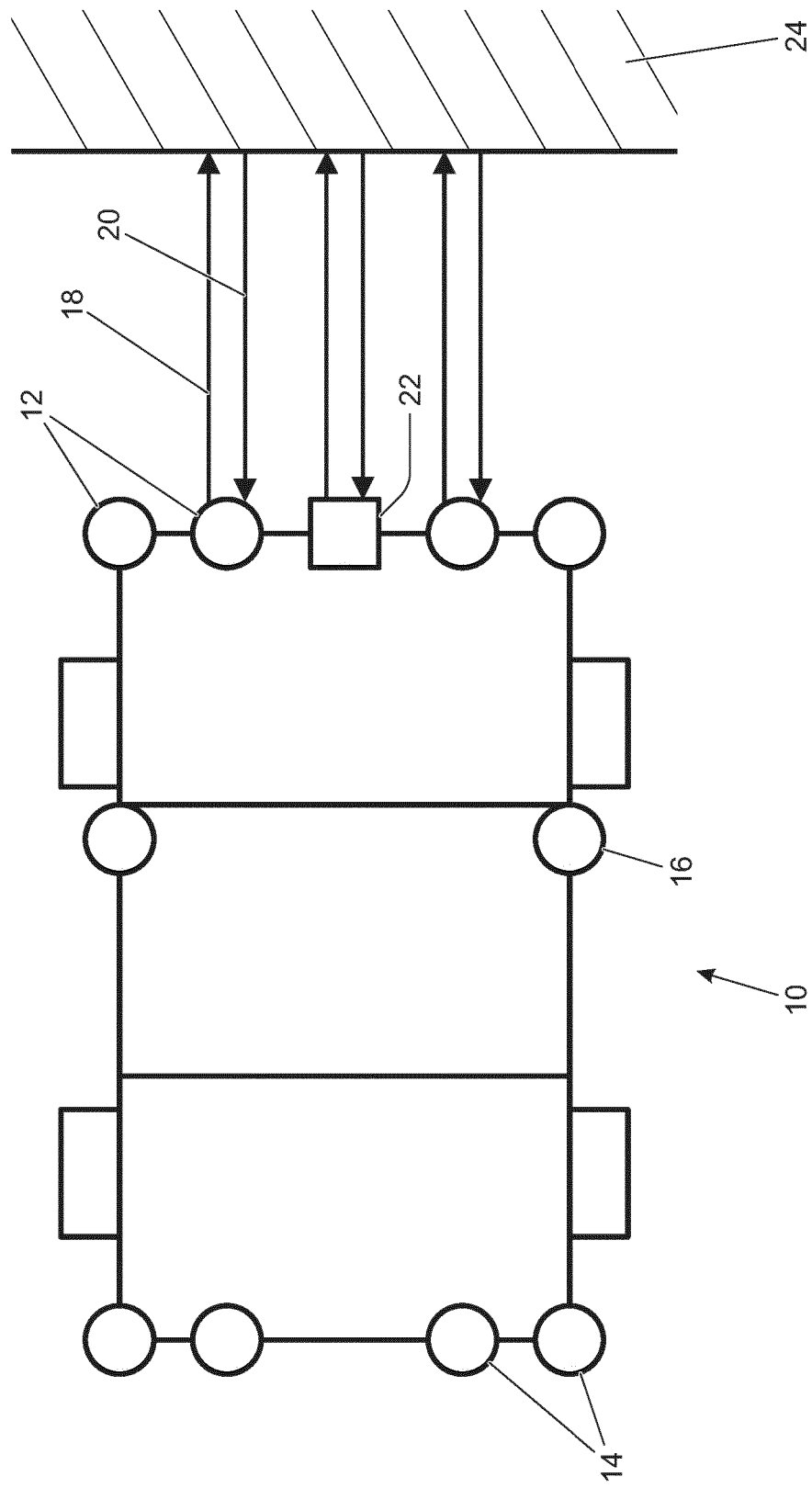
FIG. 1 is an overhead view of a vehicle and of terrain ahead of the vehicle.

FIG. 1 shows one embodiment of a vehicle 10 with two different types of sensors that collect data to be input to different systems of the vehicle. In current systems, there may be acoustic sensors positioned at the front 12, rear 14 and/or side 16 of the vehicle: commonly, acoustic sensors are used to send and receive acoustic signals to collect sensor output data to be input to, for example, parking assistance systems of the vehicle.

Typically, parking assistance systems are used to warn a vehicle user, either by visual or audible means, of the vehicle's proximity to an obstacle. In the case of an audible warning, a warning tone may sound with increasing frequency as the obstacle becomes closer to the vehicle. The acoustic sensors used for parking assistance systems are typically able to detect obstacles at short-range (0.25-1.5 meters) but at a wide angle from the direction in which the sensor is pointed. The parking assistance system may transmit acoustic pulses 18 and then receive back any reflected signal 20 from an obstacle, which may then be processed to calculate the distance between the vehicle and the obstacle.

Also in current systems, there may be a radar sensor 22 positioned at the front of the vehicle: commonly, radar sensors are used to send and receive radar signals to collect sensor output data to be input to, for example, adaptive cruise control (ACC) systems. In an ACC system, the time between a radar signal being sent and then received back is measured, and then the distance to a vehicle in front is calculated. This information is sent to other systems of the vehicle (throttle control, brake control etc.) and the necessary action is taken to maintain a constant distance to the vehicle in front. The radar sensors in an ACC system are typically able to detect an obstacle up to about 150 meters in front of the vehicle but at a narrow angle from the direction in which the sensor is pointed; other ACC systems may use shorter range wider angle radars, or a combination of both.

Radar sensors may be positioned at other locations on the vehicle to collect sensor output data to be input to, for example, blind spot detection (BSD) systems, lane departure warning systems, or speed-gun detector systems (none of which are shown). FIG. 1 also shows the terrain 24 ahead of the vehicle.

Figure 2:
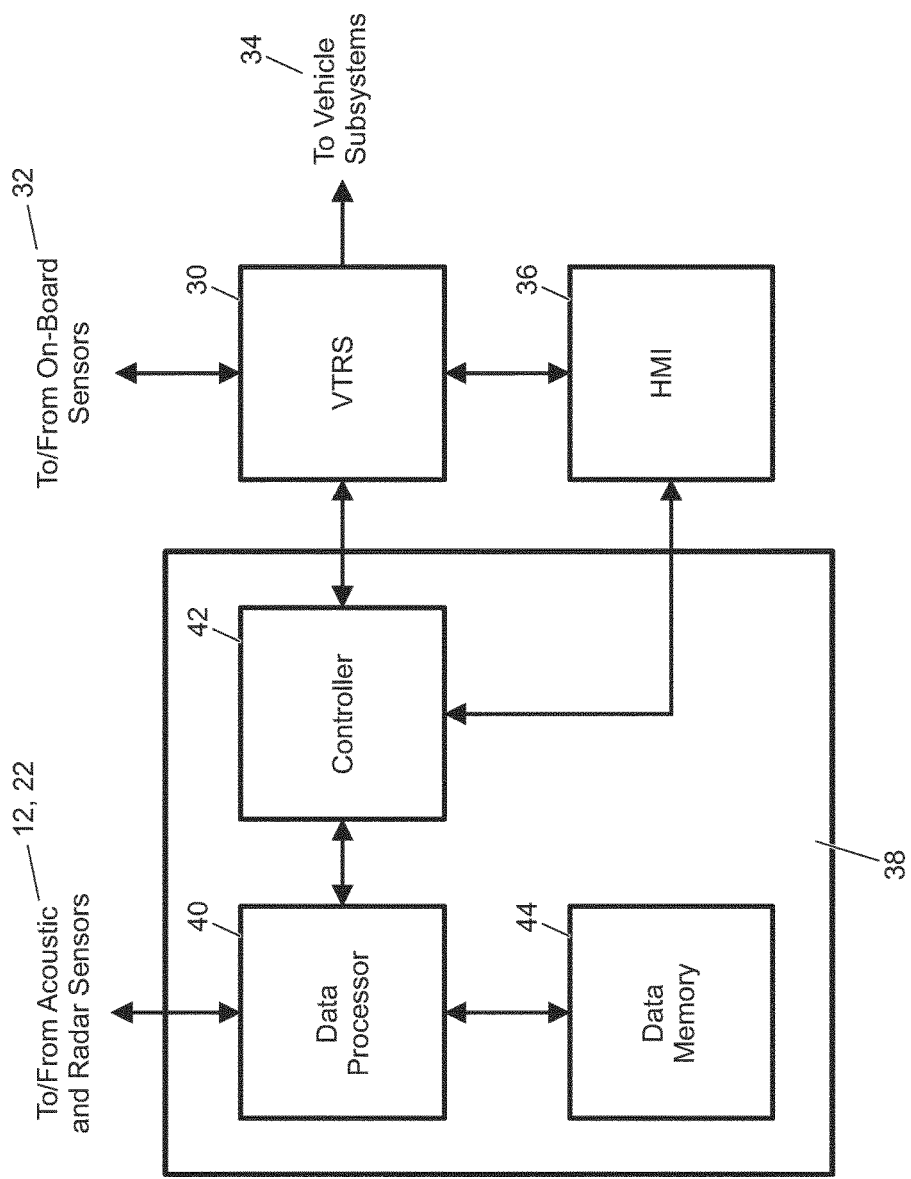
FIG. 2 is a diagram showing the component parts of a vehicle control system (VCS), together with the inputs to, and outputs from, the VCS.

Referring to FIG. 2, in some current vehicles a vehicle system is configured to improve the riding experience of the vehicle user; for example, a vehicle control system (VCS) in the form of a vehicle terrain response system (VTRS) 30, such as a Terrain Response® system, receives sensor output data from one or more on-board sensors 32 (such as a wheel speed sensor, tyre pressure sensor, vehicle speed sensor, brake pedal position sensor, suspension articulation, acceleration, wheel slip, pitch rate, and yaw rate) relating to the terrain ahead of the vehicle 10, processes the data, and sends control signals via a controller to one or more subsystems 34 (such as a suspension system, traction-control system, stability-control system, engine torque system, or ride height system) so as to allow adjustment of the setup of the vehicle 10 accordingly. The controller also communicates with a human machine interface (HMI) 36 which incorporates a display. Via the HMI display, the user receives alerts or advice, relating to a host of vehicle systems, for example, satellite navigation or in-vehicle entertainment systems. The HMI 36 typically includes a touch-screen keyboard, dial, or voice activation to enable user selection of a particular input for the various vehicle systems which can be controlled.

In a vehicle incorporating a VTRS 30, in response to a user-input via the HMI 36, a control signal is sent via a controller of the VTRS 30 to the one or more vehicle subsystems 34 to adjust the vehicle setup, according to the terrain type over which the vehicle is travelling. Alternatively, the VTRS 30 may adjust the vehicle setup automatically by sending a control signal to the vehicle subsystems 34 in response to the on-board sensor output data 32. The VTRS 30 may also send alerts to the vehicle user, via the HMI 36, to adjust his/her driving style (for example, to reduce the vehicle speed), according to the terrain type over which the vehicle is travelling. Details of how the setup may be adjusted via the VTRS 30 are described in UK patent application GB2492655.

In one embodiment of the present invention, a separate VCS 38 includes: a data processor 40 that receives sensor output data from the acoustic and radar sensors 12, 22; a VCS controller 42 for sending and receiving signals from the HMI 36 and/or VTRS 30; and a data memory 44 for storing acoustic and radar sensor output data.

The VCS 38 determines an indication of the terrain ahead of the vehicle 10 using sensor output data that is collected in real-time for a plurality of different parameters relating to characteristics of the target terrain from the acoustic and radar sensors 12, 22. The VCS controller 42 will then send a control signal to either the VTRS 30 to adjust the vehicle setup accordingly, or the HMI 36 to prompt the user to input the determined terrain type to the VTRS 30. Here and throughout, the term "determine" should be interpreted to mean "makes a best estimation of".

In more detail, the data processor 40 of the VCS 38 receives sensor output data from both the acoustic and radar sensors 12, 22. The data processor 40 is responsible for associating the received sensor output data to a particular terrain type which it does by retrieving pre-determined information from the data memory 44 for comparison with the sensor output data. Upon determination of the terrain, the data processor 40 communicates with the VCS controller 42, which is responsible for sending control signals to the HMI 36 relating to the determined terrain type. It will be appreciated that, although the processor 40 and controller 42 are shown as independent components, they may comprise a single electronic controller.

Figure 3:
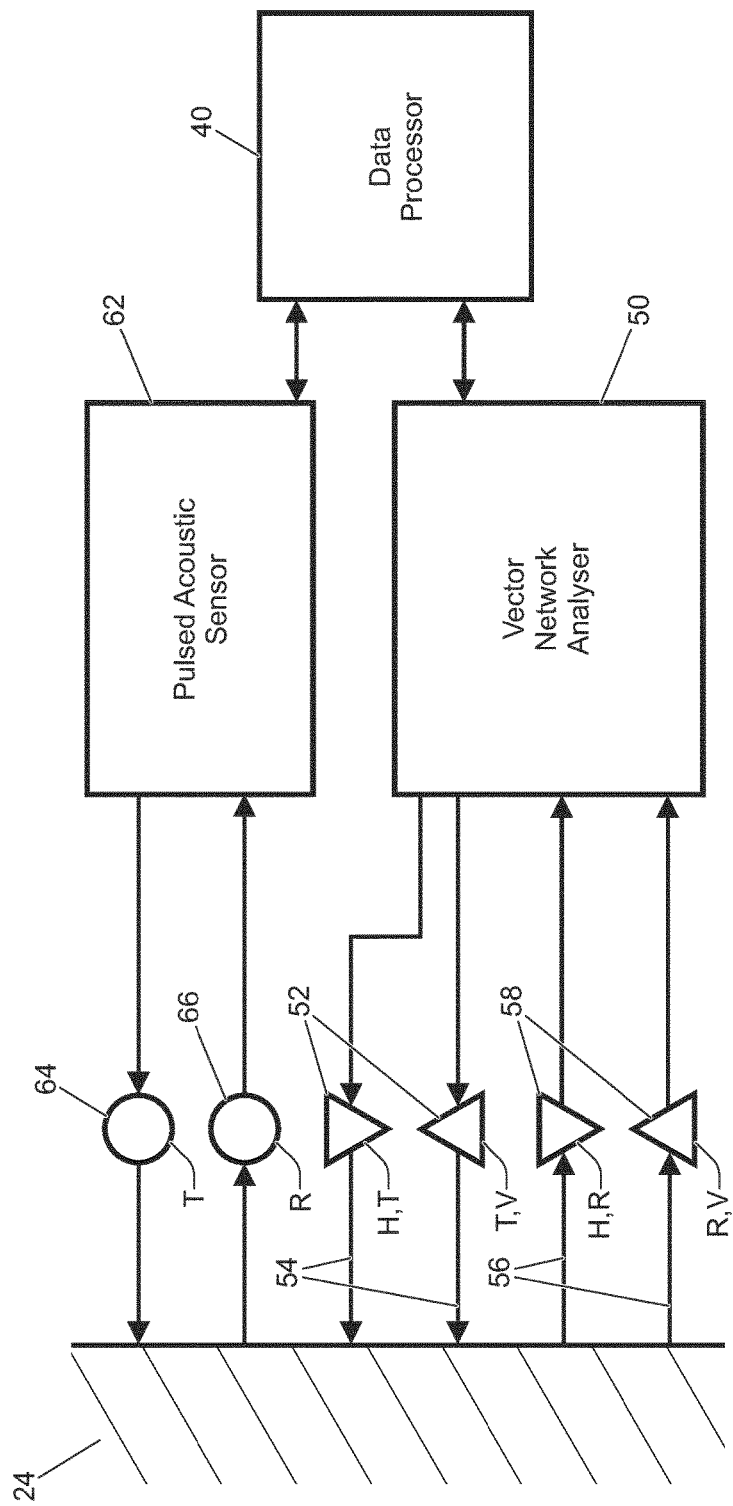
FIG. 3 is a diagram showing acoustic and radar sensors of the vehicle in FIG. 1 and means for processing output signals from those sensors.

FIG. 3 is a diagram showing acoustic and radar sensors of the vehicle 10 in FIG. 1 and the data processor 40 for processing output signals from those sensors. In this embodiment, both the radar and acoustic sensors 12, 22 are used to collect sensor output data relating to the terrain ahead of the vehicle 10. Both radar and acoustic sensor output data is used as data from one type of sensor may be advantageous over the other in certain situations.

In this embodiment, the radar signals are generated by a Vector Network Analyser (VNS) 50, transmitted at orthogonal (in particular, horizontal and vertical) polarisations by a pair of transmitting antennas 52, reflected by the terrain 24 ahead of the vehicle which alters the polarisation of the transmitted signals 54, and then the backscattered signals 56 are collected by a pair of receiving antennas 58 at orthogonal polarisations. Note that a VNA 50 is used only in the experimental stage and that a dedicated hardware sensor will eventually be used. The radar sensor units may form part of the vehicle ACC system because of the similar operation and structure of the sensor units required for both purposes.

The radar sensors 22 may be used to characterise the, for example, roughness, wave absorption, or polarisation properties of a given terrain type and, in particular, may be used to detect an area of low friction caused by, for example, water, ice, or wet grass. The roughness of a given terrain type may be characterised using radar signals by analysing the backscattering properties of the wave at different polarisations. In particular, the absolute measured values include: the vertical polarisation signal power, that is the power of a received vertically polarised signal from a vertically polarised transmitter; the horizontal polarisation signal power, that is the power of a received horizontally polarised signal from a horizontally polarised transmitter; and the cross polarisation signal power, that is the power of a received horizontally polarised signal from a vertically polarised transmitter, or vice versa. The reflection of the radar signal from the terrain causes some changes to the polarisation to produce some horizontal component from a vertically polarised transmitted signal. In this way, a measure is made of the amount of the signal power of one polarisation that has had its polarisation shifted.

The transmitting antennas 52 may be further configured to generate an elliptically polarised signal. This may be achieved by transmitting the same signal with vertical polarisation and horizontal polarisation delayed in phase by a quarter wavelength. If the signals have the same power then the generated elliptically polarised signal is a circularly polarised signal, a circularly polarised signal simply being a special case of an elliptically polarised signal.

An elliptically (or circularly) polarised signal may be generated to rotate in either a clockwise or an anticlockwise direction, depending on how the transmitting antennas 52 are arranged. A transmitting antenna capable of transmitting both clockwise and anticlockwise signals will generally consist of one vertical antenna sandwiched between two horizontal antennas (or vice versa) and each separated by a quarter wavelength. In this case, a further absolute measured value could be the power of a received anticlockwise-rotating elliptically polarised signal from a clockwise-rotating elliptically polarised signal (or vice versa), and this is referred to as the cross polarisation signal power. Note from above that "cross polarisation" may refer to either a received horizontal (or vertical) signal from a transmitted vertical (or horizontal) signal or a received clockwise- (or anticlockwise-) rotating signal from a transmitted anticlockwise- (or clockwise-) rotating signal. Similarly to above, the reflection from the terrain can change the polarisation of a clockwise- (or anticlockwise-) rotating elliptically polarised signal to produce an anticlockwise- (or clockwise-) rotating component.

The radar signals 54, 56 may be transmitted and received at a plurality of different frequencies; however, for example, in the automotive industry the currently licensed bands for short-range radar are restricted to 21.65-26.65 GHz and 76-81 GHz. Note that other unlicensed frequency bands may also be considered.

The amplitude and phase of the received signals 56 are recorded by the VNS 50. These are then processed to obtain, for example, average signal powers, or reflection from a fixed area of terrain ahead of the vehicle. Relative signal powers are analysed because they are less affected by transmitter power and distance than absolute values. Relative parameters include (but are not restricted to): the ratio of the vertical polarisation signal power to the horizontal polarisation signal power; the ratio of the horizontal polarisation signal power to the vertical polarisation signal power; and the ratio of the cross polarised signal power to the horizontal polarisation signal power. Note that absolute values of signal power can be used to provide extra data; however, these values may not be as useful as relative values of signal power.

In this embodiment, the acoustic signals are sent by a pulsed acoustic sensor 62 through a transmitting antenna 64 and the backscattered signal, received through a receiving antenna 66, is measured for energy, duration, range and/or another property of the signal by the pulsed acoustic sensor 62. The data processor 40 processes the received signal to, for example; appropriately scale the signal, to account for path loss, to average the signal in time, and/or to compare against signals in different conditions (such as different weather conditions). The acoustic sensor 62 may also measure the relative backscattered signals from several range cells over the range of the transmitted signal then analyse the characteristics of the different cells. In other words, the relative backscattered signals can be gated in time to provide swathes of data to be analysed.

The acoustic sensor units form part of the vehicle parking assistance system because of the similar operation and structure of the sensor units required for both purposes. The acoustic sensor may be used to characterise the, for example, roughness, texture, or sound absorption of a given terrain type. The acoustic sensor may also be used to measure the relative backscattered signals from several range cells over the range extent of the sensor beam and analyse the characteristics of the relative levels. The optimum frequency in terms of cost and attenuation through the atmosphere is 40-50 kHz, and acoustic sensors on current vehicles operate at typically 51.2 kHz.

At the point of vehicle manufacture, the VCS 38 goes through a calibration process whereby pre-determined data obtained from offline measurements is pre-stored on the data memory 44 of the VCS 38. The pre-determined data is for a plurality of parameters and relates to a known terrain type. The pre-determined data stored in the data memory 44 may be part of a standardised data set and/or may include empirically-gathered data. A multi-dimensional vector consisting of the parameters of the pre-determined data is stored in the data memory 44. Each set of collected data may be regarded as a data point in multi-dimensional vector space and the data points can be clustered according to the particular type of terrain they correspond to. Once calibrated, the VCS 38 is used in real-time to determine an indication of an unknown terrain type ahead of the vehicle 10. To do this, the data processor 40 analyses real-time sensor output data and compares this with pre-determined clusters of data on the data memory 44.

Figure 4:
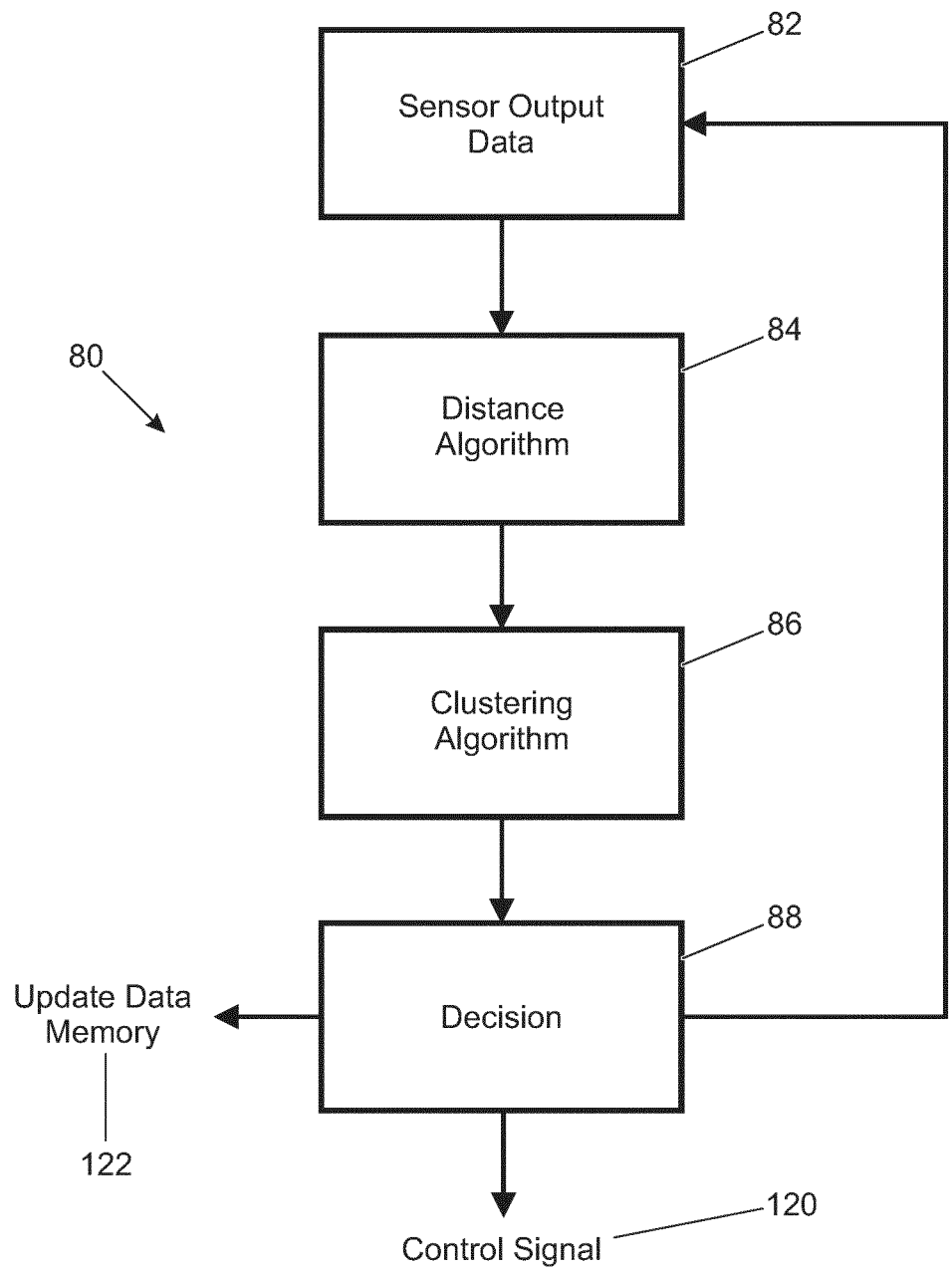
FIG. 4 is a flow diagram which illustrates a process according to an embodiment of the invention for associating sensor output data relating to the terrain ahead of the vehicle in FIG. 1 with a particular terrain type.

In order to analyse the sensor output data in real-time the data processor 40 employs a mathematical cluster model. FIG. 4 illustrates the steps undertaken by the data processor 40 during the clustering process 80 which consists of initially receiving sensor output data 82 for an unknown terrain type ahead of the vehicle 10 from the acoustic and radar sensors 12, 22 for the same parameters as those in the pre-stored multi-dimensional vector. A metric is used at step 84 to calculate the distance from the sensor output data point to each pre-determined data point in the multi-dimensional vector. A clustering algorithm is used at step 86 to decide to which pre-stored cluster the sensor output data point belongs (where each pre-stored cluster corresponds to a particular terrain type), thereby determining an indication of the terrain type at step 88.

The clustering process 80 is now described in more detail. Sensor output data 82 is collected for a plurality of parameters as described above. The parameters for which data is collected is pre-determined to be the optimal set of parameters. The optimal parameters may be regarded as those which display the greatest differences in the sensor output data 82 between different terrain types.

Figure 5:
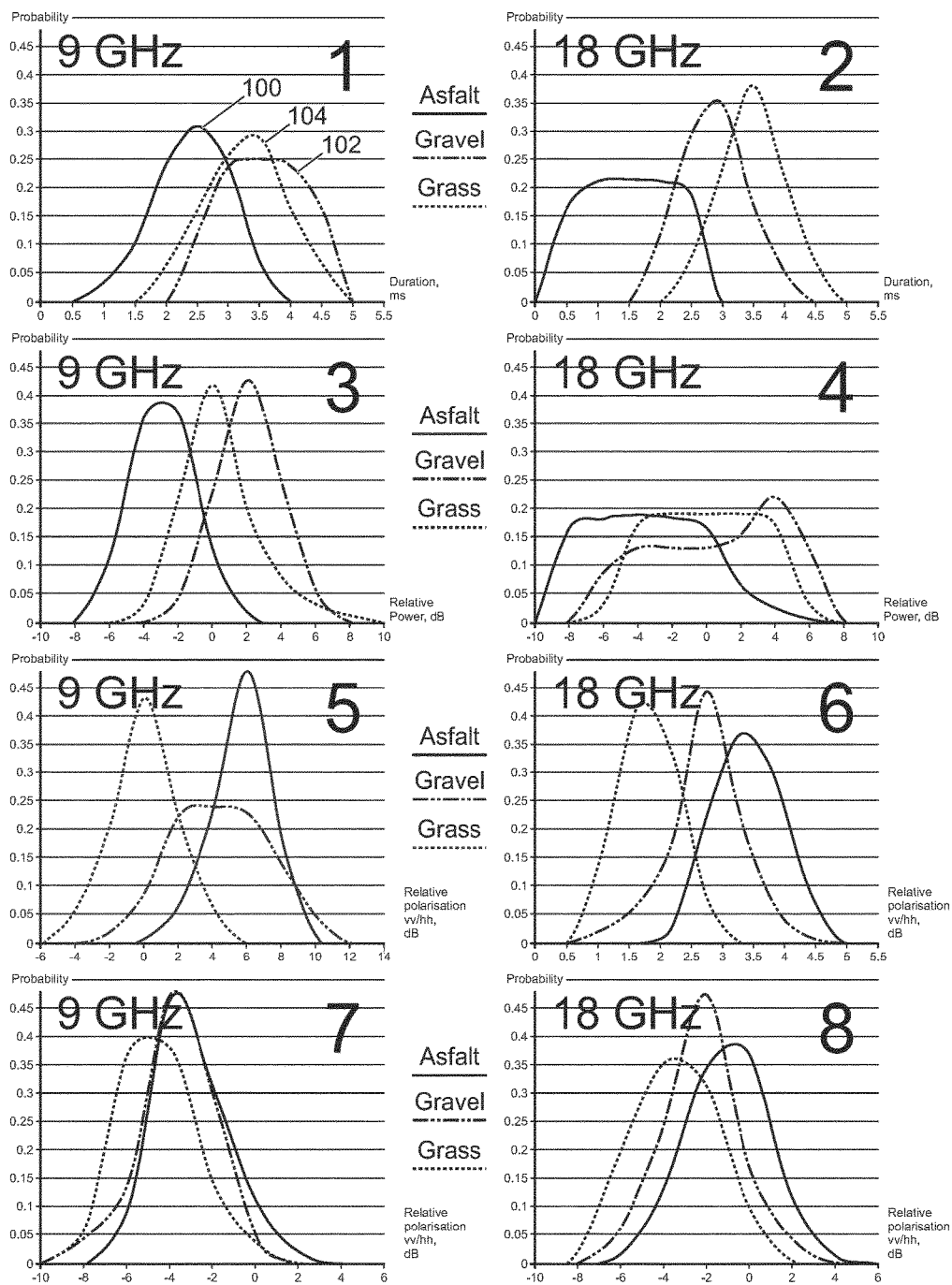
FIG. 5 shows histograms of power distribution for different parameters for two different frequencies of a received radar signal reflected from three different terrain types.

For example, FIG. 5 shows histograms of power distribution for different parameters for two different frequencies of a received radar signal for three different terrain types: in this case, asphalt 100, gravel 102 and grass 104. In particular, FIGS. 5(1) and 5(2) show the backscatter signal duration d, FIGS. 5(3) and 5(4) show the average relative power of a vertically polarised transmitted signal to a vertically polarised received signal σvv, FIGS. 5(5) and 5(6) show the ratio of the vertical polarisation signal power to the horizontal polarisation signal power pvv, and FIGS. 5(7) and 5(8) show the ratio of the cross-polarisation signal power to the horizontal polarisation signal power pvh. In addition, FIGS. 5(1), 5(3), 5(5) and 5(7) are for a 9 GHz radar signal and FIGS. 5(2), 5(4), 5(6) and 5(8) are for an 18 GHz radar signal. Data such as that shown in FIG. 5 may be used to pre-determine which parameters to include in the optimal set. This is done by considering the independence and contrast between each curve on each plot.

FIG. 6 shows a table of the optimal set of parameters of the sensor output data in FIG. 5 in the cases where the dimension of the optimal set is between two and six, and in the cases where one or both of the two radar signal frequencies are used. FIG. 6 also shows the probability that the terrain type is determined correctly in each of the above-mentioned cases. In particular, in the case where both the 9 GHz and 18 GHz radar signal is used, parameters for both frequencies appear in the optimal set 110. Further, the probability 112 that the terrain type is determined correctly is higher when parameters relating to sensor output data from both signal frequencies are used compared with when just one frequency is used. The method by which the parameters are used to determine an indication of the terrain type is described below.

At step 84 the normalised distance between the sensor output data point and each pre-determined data point is calculated. In one embodiment, a Euclidean algorithm may be used to calculate the normalised distance between each pair of data points.

As mentioned above, each pre-determined data point is associated with a particular terrain type and each set of pre-determined data points that are associated with the same terrain type may be regarded as a cluster or group. At step 86 the sensor output data point is assigned to the cluster whose characteristics most closely match those of the sensor output data point. There are several different ways in which the similarity between the characteristics of a particular cluster and of the sensor output data point may be measured. One strategy with which to determine to which particular cluster the characteristics of the sensor data point are most similar is to minimise some measure of the normalised distance between the sensor output data point and a particular cluster.

In one embodiment, a K-nearest neighbour algorithm is used to minimise the normalised distance between the sensor output data point and a particular cluster. The K-nearest neighbour algorithm is based on minimising the sum of the normalised distances from the sensor output data point to the K nearest pre-determined data points in each cluster. In particular, this may be written as $$\underset{i}{\mathrm{argmin}} \frac{\sum_{j=1}^{K} \sqrt{\sum_{l=1}^{N} (x_{ijl} - y_l)^2}}{\sum_{i=1}^{M} \sum_{j=1}^{K} \sqrt{\sum_{l=1}^{N} (x_{ijl} - y_l)^2}},$$

for i=1, 2, ..., M, where $x_{ij}=(x_{ij1}, x_{ij2}, \ldots x_{ijN})$ is the j-th closest pre-determined data point of the i-th cluster to the sensor output data point, $y=(y_1, y_2, \ldots y_N)$ is the sensor output data point, M is the number of clusters and N is the number of parameters in the optimal set. The above equation returns the number of the cluster (1, 2, ..., M) that is nearest to the sensor output data point.

A relatively small number of clusters M leads to noise having a significant effect on the result and a relatively large number of clusters M leads to the algorithm being computationally expensive.

Figure 7:
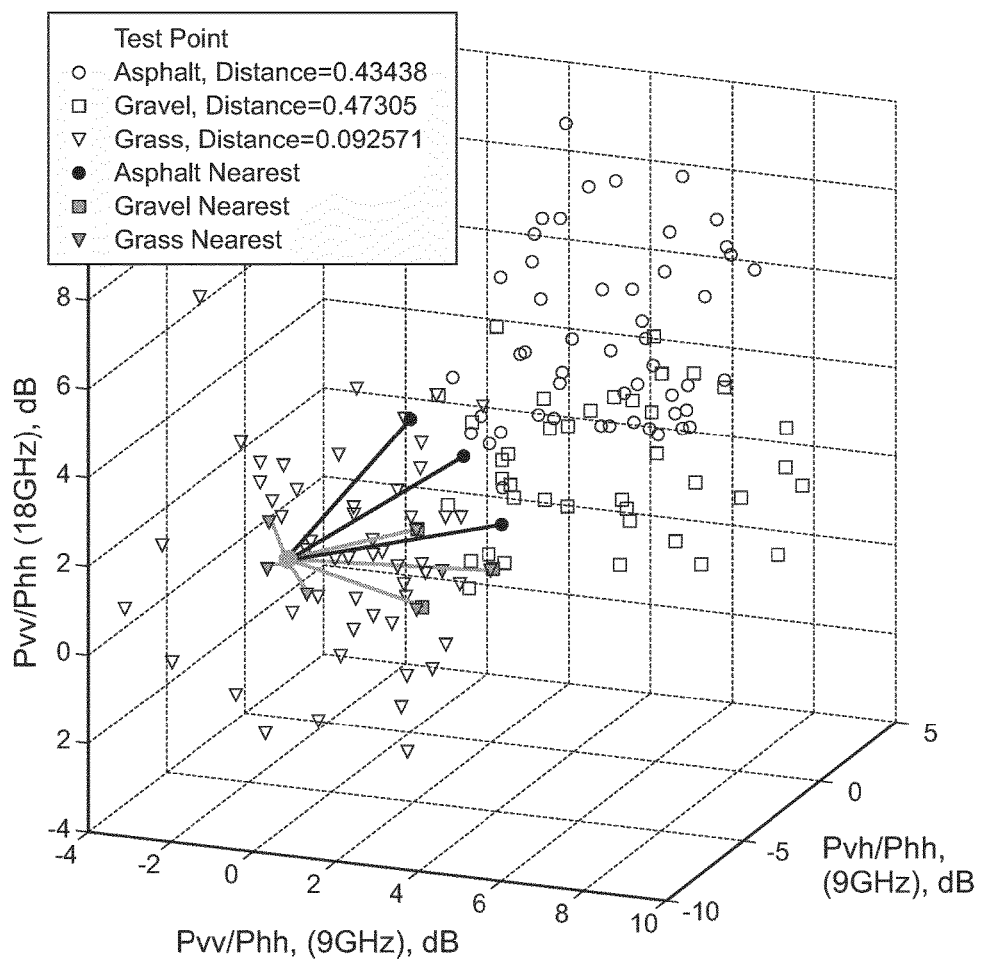
FIG. 7 shows a three-dimensional plot of parameters relating to a received radar signal from three different terrain types, and shows the Euclidean distance from a data point relating to sensor output data to the three nearest data points for each terrain type.

FIG. 7 shows an example of the K-nearest neighbour algorithm with K=3, M=3 and N=3. In particular, the three parameters in the optimal set are the ratio of the relative vertical polarisation signal power to the relative horizontal polarisation signal power for a 9 GHz signal, the ratio of the relative vertical polarisation signal power to the relative horizontal polarisation signal power for a 18 GHz signal and the ratio of the cross polarisation signal power to the relative horizontal polarisation signal power for a 9 GHz signal. The normalised Euclidean distance from the sensor output data point (labelled as the "Test Point" in FIG. 7) to each of the three nearest pre-determined data points from each cluster is shown. By inspection of FIG. 7 it is clear that the sum of the normalised Euclidean distances to the three nearest grass pre-determined data points yields the smallest value and therefore the sensor output data point is assigned to the cluster corresponding to grass.

At the decision step 88 in FIG. 4, the data processor 40 compares the determined terrain type to the terrain type for which the vehicle is currently set up to travel over. If the determined terrain type is the same as the current terrain type then the system loops back to step 82 to analyse the next set of sensor output data from the acoustic and radar sensors 12, 22. If the determined terrain type is different to the current terrain type then the data processor 40 communicates with the VCS controller 42 to send a control signal at step 120 to either the HMI 36 or directly to the VTRS 30 as described above, and then the system loops back to step 82 to analyse the next set of sensor output data from the acoustic and radar sensors 12, 22.

The data processor 40 also updates the data memory 44 at step 122 with the sensor output data 82 and determined terrain type as part of a self-learning process. In this way the VCS 38 is continuously updated and therefore the likelihood of the data processor 40 assigning the next set of sensor output data 82 to the most appropriate cluster is increased.

In an alternative embodiment, some other metric may be used at the distance algorithm step 84, for example, Minkowski distance, Hamming distance, or Chebyshev distance, all of which are well-known mathematical techniques.

In an alternative embodiment, some other clustering algorithm may be used at step 86, for example, a K-means algorithm, a classification tree algorithm, a naïve Bayes algorithm, or a support vector machine algorithm, all of which are well-known mathematical clustering algorithms.

The well-known K-means algorithm is based on each sensor output data point being assigned to the cluster with the nearest mean pre-determined data point. The mean pre-determined data point may be defined as the pre-determined data point that yields the smallest value when calculating the cumulative distance to each of the other pre-determined data points in a specific cluster. As described above, there are several different metrics that may be used to determine the distance between two data points.

The skilled reader will understand that there are many well-known mathematical clustering algorithms available that could be used rather than the ones mentioned above.

In a further embodiment, the sensor output data from the acoustic and radar sensors 12, 22 is used in conjunction with the sensor output data from the on-board sensors 32 while accounting for the spatial and/or temporal disparity between sensors receiving data relating to terrain ahead of the vehicle 10 and sensors receiving data relating to terrain over which the vehicle 10 is travelling. For example, a time delay would be introduced based on the vehicle speed to pair sensor output data from the acoustic and radar sensors 12, 22 to the automatically determined terrain type (determined using the on-board sensors 32). The acoustic and radar sensor output data and the determined terrain type are then stored in the data memory 44.

In addition, in the case where the VCS controller 42 communicates with the HMI 36 to prompt the user to input the determined terrain type to the VTRS 30, if the user over-rides the determined terrain type communicated by the VCS controller 42 and in fact inputs a different terrain type to the VTRS 30, then the acoustic and radar sensor output data that the determination was based on is input to the cluster of the terrain type that the user inputs rather than to the (incorrectly) determined cluster. This is beneficial because there may be some overlap between clusters where it is difficult to make a positive determination based on pre-determined data which is not particular to the specific geographic location in which the vehicle is normally used. Also, the use of driver allocated terrain types could better define the clusters for the specific location in which the vehicle is being driven and result in more accurate future system performance. Note that this user over-ride approach may also be used in the case where the VCS controller 42 communicates directly with the VTRS 30 to automatically adjust the vehicle setup. Each data point, labelled with a particular terrain type, is then sent to the data memory 44. The VCS 38 is then ready to undertake a clustering process 80 as shown in FIG. 4 (and described above).

In a further embodiment, external data may be used to eliminate certain clusters when deciding to which cluster a particular data point belongs. For example, if an external temperature sensor determines that the external temperature is 30 degrees Celsius, then the cluster corresponding to snow can safely be eliminated from consideration.

It will be appreciated by a person skilled in the art that the invention could be modified to take many alternative forms without departing from the scope of the appended claims.

Further aspects of the present invention are set out in the following numbered Clauses:

Clause 1: A system for use in a vehicle for determining an indication of the type of terrain in the vicinity of the vehicle, the system comprising; a receiver to receive sensor output data from at least one vehicle-mounted sensor which is configured to receive a reflected signal from the terrain; and a processor to calculate at least two parameters from the sensor output data, to convert the at least two parameters to a data point for a cluster model comprising a plurality of clusters of pre-determined data points, wherein each cluster corresponds to a different terrain type, and to define to which one of the clusters the data point belongs, so as to determine an indication of the terrain type.

Clause 2: A system according to Clause 1, comprising a controller to output a control signal to one or more vehicle systems to automatically adjust the setup of at least one vehicle subsystem according to the determined terrain type.

Clause 3: A system according to Clause 1, wherein the pre-determined data points comprise empirically-gathered data.

Clause 4: A system according to Clause 1, wherein the pre-determined data points comprise a standardised data set.

Clause 5: A system according to Clause 1, further comprising a communication device to enable communication of the determined terrain type to the user.

Clause 6: A system according to Clause 5, wherein the communication device is a human machine interface (HMI).

Clause 7: A system according to Clause 5, wherein the communication device is further configured to enable user-input of a terrain type following a determination of the terrain type by the user.

Clause 8: A system according to Clause 7, the processor being configured to compare the determined terrain type with the terrain type determined by the user as part of a self-learning process.

Clause 9: A system according to Clause 1, comprising a storage device to store the at least two parameters together with the corresponding determined terrain type as part of a self-learning process.

Clause 10: A system according to Clause 1, the processor being configured to compare the determined terrain type with a terrain type as determined from one or more other vehicle-mounted sensor.

Clause 11: A system according to Clause 1, wherein the receiver is configured to receive a reflected radar signal from the terrain ahead of the vehicle.

Clause 12: A system according to Clause 11, wherein the receiver is configured to receive the reflected radar signal at a plurality of radar signal frequencies.

Clause 13: A system according to Clause 11, wherein the receiver is configured to receive a signal in the form of a received horizontally polarised signal representative of power in a received horizontal polarisation component of a radar signal reflected from the terrain ahead of the vehicle and/or to receive a vertically polarised signal representative of power in a received vertical polarisation component of a radar signal reflected from the terrain ahead of the vehicle.

Clause 14: A system according to Clause 13, wherein the processor is configured to determine one or more of: a horizontal polarisation power signal, that is the power of the received horizontally polarised signal from a horizontally polarised transmitter; a vertical polarisation power signal, that is the power of the received vertically polarised signal; and a cross polarisation power signal, that is the power of the received horizontally polarised signal from a vertically polarised transmitter or the power of the received vertically polarised signal from a horizontally polarised transmitter.

Clause 15: A system according to Clause 11 wherein the receiver is configured to receive a signal in the form of a received elliptically polarised signal or a received circularly polarised signal.

Clause 16: A system according to Clause 15, wherein the processor is configured to determine a cross polarisation power signal, that is the power of a received clockwise-rotating elliptically polarised signal or a received clockwise-rotating circularly polarised signal from a transmitted anti-clockwise-rotating elliptically polarised signal or a transmitted anticlockwise-rotating circularly polarised signal, or the power of a received anticlockwise-rotating elliptically polarised signal or a received anticlockwise-rotating circularly polarised signal from a transmitted clockwise-rotating elliptically polarised signal or a transmitted clockwise-rotating circularly polarised signal.

Clause 17: A system according to Clause 14, wherein the processor is configured to determine the ratio of any two of: the horizontal polarisation power signal; the vertical polarisation power signal; and the cross polarisation power signal.

Clause 18: A system according to Clause 1, wherein the receiver is configured to receive a reflected acoustic signal from the terrain ahead of the vehicle at one or more acoustic signal frequencies.

Clause 19: A system according to Clause 18 when dependent on Clause 13, wherein the processor is configured to determine a ratio of the acoustic power signal and one or more of: the horizontal polarisation power signal; the vertical polarisation power signal; and the cross polarisation power signal.

Clause 20: A system according to Clause 1, wherein the processor is configured to calculate the distance between the data point relating to the at least two parameters and at least two of the pre-determined data points.

Clause 21: A system according to Clause 20, wherein the processor includes a Euclidean algorithm.

Clause 22: A system according to Clause 1, wherein the processor includes one of: a 'k-nearest neighbour' algorithm; a 'k-means' algorithm; a 'classification tree' algorithm; a 'naïve Bayes' algorithm; and a 'support vector machine' algorithm.

Clause 23: A system according to Clause 1, wherein the processor uses external data to eliminate certain clusters from consideration.

Clause 24: A method for use in a vehicle for determining an indication of the type of terrain in the vicinity of the vehicle, the method comprising; receiving sensor output data from at least one vehicle-mounted sensor which is configured to receive a reflected signal from the terrain; calculating at least two parameters of the sensor output data; converting the at least two parameters to a data point for a cluster model comprising a plurality of clusters of pre-determined data points, wherein each cluster corresponds to a different terrain type; and assigning the data point to one of the clusters so as to determine the terrain type.

Clause 25: A method according to Clause 24, comprising outputting a control signal to one or more vehicle systems to automatically adjust the setup of at least one vehicle sub-system according to the determined terrain type.

Clause 26: A method according to Clause 24, wherein the pre-determined data points comprise empirically-gathered data.

Clause 27: A method according to Clause 24, wherein the pre-determined data points comprise a standardised data set.

Clause 28: A method according to Clause 24, further comprising enabling communication of the determined terrain type to the user.

Clause 29: A method according to Clause 27, comprising enabling user-input of a terrain type following a determination of the terrain type by the user.

Clause 30: A method according to Clause 29, comprising comparing the determined terrain type with the terrain type determined by the user as part of a self-learning process.

Clause 31: A method according to Clause 24, comprising storing the at least two parameters together with the corresponding determined terrain type as part of a self-learning process.

Clause 32: A method according to Clause 24, comprising comparing the determined terrain type with a terrain type as determined from one or more other vehicle-mounted sensor.

Clause 33: A method according to Clause 24, comprising receiving a reflected radar signal from the terrain ahead of the vehicle.

Clause 34: A method according to Clause 33, comprising receiving the reflected radar signal at a plurality of radar signal frequencies.

Clause 35: A method according to Clause 34, comprising receiving a signal in the form of a received horizontally polarised signal representative of power in a received horizontal polarisation component of a radar signal reflected from the terrain ahead of the vehicle and/or to receive a vertically polarised signal representative of power in a received vertical polarisation component of a radar signal reflected from the terrain ahead of the vehicle.

Clause 36: A method according to Clause 35, comprising determining one or more of: a horizontal polarisation power signal, that is the power of the received horizontally polarised signal from a horizontally polarised transmitter; a vertical polarisation power signal, that is the power of the received vertically polarised signal from a vertically polarised transmitter; and a cross polarisation power signal, that is the power of the received horizontally polarised signal from the vertically polarised transmitter or the power of the received vertically polarised signal from the horizontally polarised transmitter.

Clause 37: A method according to Clause 33, comprising receiving a signal in the form of a received clockwise-rotating or anticlockwise-rotating elliptically polarised signal, or a received clockwise-rotating or anticlockwise-rotating circularly polarised signal.

Clause 38: A method according to Clause 37, comprising determining a cross polarisation power signal, that is the power of the received clockwise-rotating elliptically polarised signal or the received clockwise-rotating circularly polarised signal from a transmitted anticlockwise-rotating elliptically polarised signal or a transmitted anticlockwise-rotating circularly polarised signal, or the power of the received anticlockwise-rotating elliptically polarised signal or the received anticlockwise-rotating circularly polarised signal from a transmitted clockwise-rotating elliptically polarised signal or a transmitted clockwise-rotating circularly polarised signal.

Clause 39: A method according to Clause 36, comprising determining the ratio of any two of: the horizontal polarisation power signal; the vertical polarisation power signal; and the cross polarisation power signal.

Clause 40: A method according to Clause 24, comprising receiving a reflected acoustic signal from the terrain ahead of the vehicle at one or more acoustic signal frequencies.

Clause 41: A method according to Clause 40 when dependent on Clause 35, comprising determining a ratio of the acoustic power signal and one or more of: the horizontal polarisation power signal; the vertical polarisation power signal; and the cross polarisation power signal.

Clause 42: A method according to Clause 24, comprising calculating the distance between the data point relating to the at least two parameters and at least two of the pre-determined data points.

Clause 43: A method according to Clause 24, comprising using one of: a 'k-nearest neighbour' algorithm; a 'k-means' algorithm; a 'classification tree' algorithm; a 'naïve Bayes' algorithm; and a 'support vector machine' algorithm, to determine to which one of the clusters the data point belongs.

Clause 44: A method according to Clause 24, comprising using external data to eliminate certain clusters from consideration to determine to which one of the clusters the data point belongs.

Clause 45: A data memory containing a computer readable code for performing the method according to Clause 24.

Clause 46: A vehicle controller for determining an indication of the type of terrain in the vicinity of the vehicle, the controller comprising: an input to receive sensor output data from at least one vehicle-mounted sensor which is configured to receive a reflected signal from the terrain; a processor to calculate at least two parameters from the sensor output data; wherein the processor converts the at least two parameters to a data point for a cluster model stored in memory of or associated with the controller, the cluster model comprising a plurality of clusters of pre-determined data points, wherein each cluster corresponds to a different terrain type, and the processor defines to which one of the clusters the data point belongs, to thereby determine an indication of the terrain type.

Clause 47: A vehicle comprising a system according to Clause 1.

Clause 48: A vehicle comprising a controller according to Clause 45.

The invention claimed is:

1. A system for use in a vehicle for determining an indication of the type of terrain in the vicinity of the vehicle, the system comprising:
   a receiver configured to receive sensor output data, the sensor output data comprising radar sensor output data from a vehicle-mounted radar sensor which is configured to receive a reflected radar signal from the terrain, and the sensor output data comprising acoustic sensor output data from a vehicle-mounted acoustic sensor which is configured to receive a reflected acoustic signal from the terrain; and
   a processor configured to:
   calculate values of at least two parameters based on the received sensor output data, wherein each parameter is indicative of a property of the type of terrain in the vicinity of the vehicle, wherein the property includes at least one of roughness, polarisation, texture, wave absorption and sound absorption;
   convert the at least two parameter values to a measured multi-dimensional data point;
   create a cluster model comprising a plurality of clusters each comprising pre-determined multi-dimensional data points for the same parameters as the at least two calculated parameter values, and wherein each cluster corresponds to a different terrain type;
   calculate a distance metric for each cluster indicative of a normalised distance between the measured multi-dimensional data point and the respective cluster; and,
   apply a clustering algorithm to the cluster model in dependence on the calculated distance metrics to assign the measured multi-dimensional data point to one of the plurality of clusters so as to determine the terrain type.

2. A system according to claim 1, comprising an output to output a control signal to one or more vehicle systems to automatically adjust the setup of at least one vehicle sub-system according to the determined terrain type.

3. A system according to claim 1, wherein the pre-determined multi-dimensional data points comprise one or more of empirically-gathered data and a standardised data set.

4. A system according to claim 1, further comprising a human machine interface configured to enable communication of the determined terrain type to the user and to enable user-input of a terrain type following a determination of the terrain type by the user, the processor being programmed to compare the determined terrain type with the terrain type determined by the user as part of a self-learning process.

5. A system according to claim 1, comprising a memory to store the at least two parameter values together with the corresponding determined terrain type as part of a self-learning process.

6. A system according to claim 1, wherein the processor compares the determined terrain type with a terrain type as determined from one or more other vehicle-mounted sensor.

7. A system according to claim 1, wherein the receiver receives the reflected radar signal at a plurality of radar signal frequencies.

8. A system according to claim 1, wherein the receiver receives a signal in the form of a received horizontally polarised signal representative of power in a received horizontal polarisation component of a radar signal reflected from the terrain ahead of the vehicle and/or to receive a vertically polarised signal representative of power in a received vertical polarisation component of a radar signal reflected from the terrain ahead of the vehicle.

9. A system according to claim 8, wherein the processor determines one or more of: a horizontal polarisation power signal, that is the power of the received horizontally polarised signal from a horizontally polarised transmitter; a vertical polarisation power signal, that is the power of the received vertically polarised signal; and a cross polarisation power signal, that is the power of the received horizontally polarised signal from a vertically polarised transmitter or the power of the received vertically polarised signal from a horizontally polarised transmitter.

10. A system according to claim 1, wherein the receiver receives a signal in the form of a received elliptically polarised signal or a received circularly polarised signal.

11. A system according to claim 10, wherein when the receiver receives the signal in the form of a received elliptically polarised signal the processor determines a cross polarisation power signal, that is, the power of a received clockwise-rotating elliptically polarised signal from a transmitted anticlockwise-rotating elliptically polarised signal, or the power of a received anticlockwise-rotating elliptically polarised signal from a transmitted clockwise-rotating elliptically polarised signal.

12. A system according to claim 9, wherein the processor determines the ratio of any two of: the horizontal polarisation power signal; the vertical polarisation power signal; and the cross polarisation power signal.

13. A system according to claim 1, wherein the receiver receives a reflected acoustic signal from the terrain ahead of the vehicle at one or more acoustic signal frequencies.

14. A system according to claim 13 wherein the receiver receives a signal in the form of a received horizontally polarised signal representative of power in a received horizontal polarisation component of a radar signal reflected from the terrain ahead of the vehicle and a vertically polarised signal representative of power in a received vertical polarisation component of a radar signal reflected from the terrain ahead of the vehicle, wherein the processor determines a ratio of the acoustic power signal and one or more of: the horizontal polarisation power signal; the vertical polarisation power signal; and the cross polarisation power signal.

15. A system according to claim 1, wherein the processor uses external data to eliminate certain clusters from consideration.

16. A method for use in a vehicle for determining an indication of the type of terrain in the vicinity of the vehicle, the method comprising:
receiving sensor output data, the sensor output data comprising radar sensor output data from at least one vehicle-mounted radar sensor which is configured to receive a reflected radar signal from the terrain, and the sensor output data comprising acoustic sensor output data from a vehicle-mounted acoustic sensor which is configured to receive a reflected acoustic signal from the terrain at one or more acoustic signal frequencies;
calculating values of at least two parameters based on the received sensor output data, wherein each parameter is indicative of a property of the type of terrain in the vicinity of the vehicle, and wherein the property includes at least one of roughness, polarisation, texture, wave absorption and sound absorption;
converting the at least two parameter values to a measured multi-dimensional data point;
creating a cluster model comprising a plurality of clusters each comprising pre-determined multi-dimensional data points for the same parameters as the at least two calculated parameter values, and wherein each cluster corresponds to a different terrain type;
calculating a distance metric for each cluster indicative of a normalised distance between the measured multi-dimensional data point and the respective cluster; and
applying a clustering algorithm to the cluster model in dependence on the calculated distance metrics to assign the measured multi-dimensional data point to one of the clusters so as to determine the terrain type.

17. A method according to claim 16, comprising outputting a control signal to one or more vehicle systems to automatically adjust the setup of at least one vehicle subsystem according to the determined terrain type.

18. A vehicle controller for determining an indication of the type of terrain in the vicinity of the vehicle, the controller comprising:
an input means to receive sensor output data, the sensor output data comprising radar sensor output data from at least one vehicle-mounted radar sensor which is configured to receive a reflected radar signal from the terrain, and the sensor output data comprising acoustic sensor output data from a vehicle-mounted acoustic sensor which is configured to receive a reflected acoustic signal from the terrain;
a processor configured to:
calculate values of at least two parameters based on the received sensor output data; wherein each parameter is indicative of a property of the type of terrain in the vicinity of the vehicle, and wherein the property includes at least one of roughness, polarisation, texture, wave absorption and sound absorption,
convert the at least two parameter values to a measured multi-dimensional data point;
create a cluster model stored in memory of or associated with the controller, the cluster model comprising a plurality of clusters each comprising pre-determined multi-dimensional data points for the same parameters as the at least two calculated parameter values, and wherein each cluster corresponds to a different terrain type;
calculate a distance metric for each cluster indicative of a normalised distance between the measured multi-dimensional data point and the respective cluster; and
apply a clustering algorithm to the cluster model in dependence on the calculated distance metrics to define to which one of the clusters the measured multi-dimensional data point belongs, to thereby determine an indication of the terrain type.

19. A non-transient data memory containing a computer readable code for performing the method according to claim 16.

20. A vehicle comprising a system according to claim 1.

* * * * *